United States Patent [19]

Taniguchi

[11] Patent Number: 5,157,115
[45] Date of Patent: Oct. 20, 1992

[54] REGULATION OF EXPRESSION

[76] Inventor: Tadatsugu Taniguchi, Mihogaoka 19, A-207, Ibaraki-shi, Osaka 567, Japan

[21] Appl. No.: 439,663

[22] Filed: Nov. 22, 1989

[30] Foreign Application Priority Data

Nov. 25, 1988 [GB] United Kingdom ............... 8827592

[51] Int. Cl.$^5$ ........................................... C07H 17/00
[52] U.S. Cl. .................................................... 536/27
[58] Field of Search ........................................ 536/27

[56] References Cited

FOREIGN PATENT DOCUMENTS

WO85/05636 12/1985 PCT Int'l Appl. .
WO87/03451 6/1987 PCT Int'l Appl. .
WO87/07300 12/1987 PCT Int'l Appl. .

OTHER PUBLICATIONS

T. Fujita, et al., "Structure of the human interleukin 2 gene" Proc. Natl. Acad. Sci 80:7437, 1983.
T. Fujita, et al., "Regulation of human interleukin-2 gene" Cell, 46:401-407, 1986.
Böhnlein et al., The Same Inducible Nuclear Proteins Regulates Mitogen Activation of Both the Interleukin-2 Receptor-Alpha Gene and Type 1 HIV. Cell, 53:827-836 (1988).
Cross et al., Regulation of the Human Interleukin-2 Receptor $\alpha$ Chain Promoter: Activation of a Nonfunctional Promoter by the Transactivator Gene of HTLV-1, Cell, 49:47-56 (1987).
Leung et al., HTLV-1 Transactivator Induces Interleukin-2 Receptor Expression Through An NF-kB--Like Factor. Nature, 333:776-778 (1988).
Maruyama et al., Evidence for Aberrant Activation of the Interleukin-2 Autocrine Loop by HTLV-1 Encoded p40$^x$ and T3/Ti Complex Triggering. Cell, 48:343-350 (1987).
Miyatake et al., Activation of T Cell-Derived Lymphokine Genes in T Cells and Fibroblasts: Effects of Human T Cell Leukemia Virus Type I p40$^x$ Protein . . . , Nucleic Acid Research, 16:(14)6547-6566 (1988).
Nabel et al., An Inducible Transcription Factor Activates Expression of Human Immunodeficiency Virus in T Cells, Nature, 326:711-713 (1987).
Shaw et al., Identification of a Putative Regulator of Early T Cell Activation Genes, Science, 241:202-205 (1988).
Siekevitz et al., Activation of the HIV-1 by T Ce.1 Mitogens and the Trans-Activator Protein of HTLV-I, Science, 328:1575-1578 (1987).
Siekevitz et al., Activation of Interleukin 2 and Interleukin 2 Receptor (Tac) Promoter Expression by the Trans-activator (Tat) Gene Product of Human . . . , Proc. Natl. Acad. Sci. USA, 84:5389-5393 (1987).
Stein et al., Antisense Compounds: Potential Role in Cancer Therapy, Important Adv. Oncol., (U.S.A.), pp. 79-97 (1989).
Siebenlist, V. et al., Mol. Cell. Biol. 6:3042-3049 (1986).
Franza, Jr., B. R. et al., Nature 330: 391-395 (1987).
The European Search Report for the corresponding European application No. 89121590.7.

Primary Examiner—John W. Rollins
Attorney, Agent, or Firm—Sterne, Kessler, Goldstein & Fox

[57] ABSTRACT

The inhibition or control of expression of IL-2 or IL-2$\alpha$ genes, and the inhibition or control of fundamental cellular processes responsible for retroviral replication, in particular HIV-I and HTLV-I DNA molecules, are disclosed. The invention is directed to nucleic acids or nucleic acid compositions which competitively bind regions of the IL-2 or IL-2$\alpha$ genes corresponding to their respective transcription factors. DNA or RNA fragments spanning the following regions in the IL-2 gene are shown to be effective: $-195$ to $-204$; $-115$ to $-164$; and $-165$ to $-222$. DNA or RNA fragments spanning the following regions in the IL-2$\alpha$ gene are shown to be effective: $-62$ to $-71$; and $-32$ to $-86$. Compositions comprising combinations of these fragments are also disclosed.

22 Claims, 3 Drawing Sheets

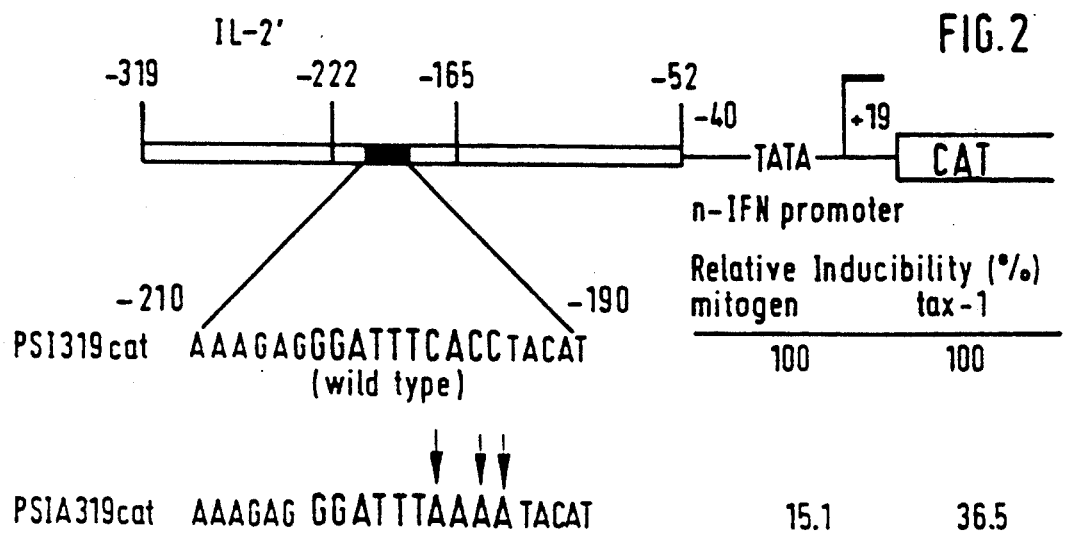
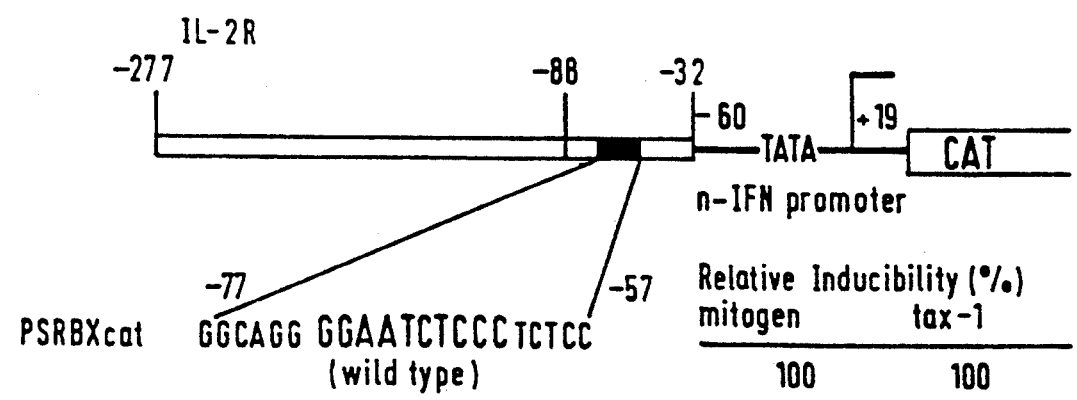
FIG. 2

REGULATION OF EXPRESSION

FIELD OF THE INVENTION

The invention relates to the inhibition of expression of Interleukin-2 (IL-2) or Interleukin-2 α receptor (IL-2Rα) genes, or the inhibition of retrovirus replication. In particular, the invention is directed to a method for inhibiting HIV-1 and/or HTLV-I using DNA or RNA fragments or compositions thereof which bind to transcription factors responsible for retroviral replication.

BACKGROUND OF THE INVENTION

Interleukin-2 (IL-2) plays an essential role in the clonal expansion of antigen-activated T-lymphocytes (T cells). In fact, the gene expression of both IL-2 and IL-2 α receptor (IL-2R α, p55, CD25) is transiently induced by antigen. Hence both the ligand and the receptor genes appear to be regulated in a coordinated manner to ensure a controlled clonal proliferation (Smith, K. A., Ann. Rev. Immunol. 2:319–334, (1984), Grene, W. C. & Leonard, W. J., Ann. Rev. Immunol. 4:69–95 (1986) and Taniguchi, T., Ann. Rev. Immunol. 6:439–464 (1980)).

The activation of IL-2 and the positive regulation of retroviral LTR-regions (HIV) have been described (Crabtree, G. R. et al., Science, July 1988). Four regulatory sequences were identified. Two regulation sequences for T-cell activation were found to span between −288 to −267 and −263 to −290 and were named "antigen receptor responsive elements" (ARRE 1 and 2). The factor that binds to ARRE 2 in Jurkat cells was named "nuclear factor of activated T cells" (NFAT). The formation of the factor was determined to be dependent upon protein biosynthesis. Studies have shown that NFAT-1 binds to the HIV-1-LTR region from −342 to −154. Various different factors are thought to bind to ARRE 1.

The nucleotide sequence of HIV-1 (Stareich, et al., Science 227:538–540 (1985)); HTLV-I (Seiki, et al., Proc. Natl. Acad. Sci., USA 80:3618–3622 (1983)); IL-2 (Fujita, et al., Proc. Natl. Acad. Sci., USA 80:7437–7441 (1983)); and IL-2R α chain (Cross, et al., Cell 49:47–56 (1987)) have previously been described.

NOTE

The numbering of the nucleotides for the IL-2R α gene used in this application is based on the designation of the nucleotide corresponding to the most upstream cap site as +1 (see Hasagawa et al., "Structure and regulation of the genes encoding interleukin-2 and its receptor. In Regulation of Immune Gene Expression, M. Feldman and A. McMichael, eds (New York: The Humana Press), pp. 85–93 (1986) and Maruyama et al., Cell, Vol. 48, 343–350, Jan. 30, 1987, and Cross et al., Cell, 49, 47–56, 1987 at page 56 "Note added in Proof").

SUMMARY OF THE INVENTION

To elucidate the mechanism(s) of the coordinated gene expression for IL-2 and IL-2R α, the inventors have investigated for the presence of potential transcription factors that specifically interact with DAN regulatory elements. As a result of these experiments the inventors have surprisingly found three such regulator (transcription) factors as well as two regulatory sequences in the IL-2 gene and an upstream regulatory sequence (element) in the IL-2R α gene. The inventors have also unexpectedly discovered that recognition sites in HIV-1 and HTLV-I, c-fos and some of the lymphokines were homologous to one of the regulatory sequences of the IL-2 gene.

The present invention therefore relates to the inhibition or control of the IL-2 and IL-2R α genes and to the control or inhibition of fundamental cellular processes responsible for retrovirus replication, in particular HIV-1 and HTLV-I. The present invention is directed to nucleic acid or nucleic acid compositions including double stranded DNA, single stranded DNA or RNA which competitively bind to transcription factors. These transcription factors are required for the expression of IL-2 and IL-2R α as well as for retroviral replication. By competitively binding these transcription factors with DNA or RNA fragments or compositions thereof, the present invention makes it possible to regulate or inhibit the function of these factors by limiting their availability in vivo or in vitro.

The present invention thus relates to the inhibition or control of expression of IL-2 or IL-2R α genes, or the inhibition or control of retrovirus replication. In particular, the invention is directed to a method for inhibiting retroviral replication thereby providing a method of treating HIV-1 or HTLV-I infection in vivo.

The invention is specifically directed to: a DNA fragment of the IL-2 gene, spanning from −195 to −204 of the genetic sequence of said gene; a DNA fragment of the IL-2 gene, spanning from −115 to −164 of the genetic sequence of said gene; a DNA fragment of the IL-2 gene, spanning from −165 to −222 of the genetic sequence of said gene; a DNA fragment of the IL-2R α gene, spanning from −62 to −71 of the genetic sequence of said gene; and a DNA fragment of the IL-2R α gene, spanning from −32 to −86 of the genetic sequence of said gene.

The invention is also directed to a DNA molecule comprising two fragments of the IL-2 gene, said first fragment spanning from −195 to −204 of the genetic sequence of said gene, and said second fragment spanning from −115 to −164 of the genetic sequence of said gene but specifically lacking a substantial portion of the fragment spanning from −165 to −194 of the genetic sequence of said gene. These two fragments may further comprising a fragment of the IL-2R α gene, said fragment spanning from −62 to −71 of the genetic sequence of said gene.

The present invention further relates to: a DNA molecule comprising a fragment of the IL-2 gene and a fragment of the IL-2R α gene, said first fragment spanning from −195 to −204 of the genetic sequence of said IL-2 gene, and said second fragment spanning from −62 to −71 of the genetic sequence of said IL-2R α gene; a DNA molecule comprising a fragment of the IL-2 gene and a fragment of the IL-2R α gene, said first fragment spanning from −115 to −164 of the genetic sequence of said IL-2 gene, and said second fragment spanning from −62 to −71 of the genetic sequence of said IL-2R α gene; and a DNA molecule comprising a fragment of the IL-2 gene and a fragment of the IL-2R α gene, said first fragment spanning from 165 to −222 of the genetic sequence of said IL-2 gene, and said second fragment spanning from −32 to −86 of the genetic sequence of said IL-2R α gene.

Thus, the nucleotides of the present invention make it possible to competitively bind cellular transcription factors in vivo or in vitro. By competitively binding these transcription factors in vivo, this invention provides a method to inhibit retroviral replication in the cell. Therefore, one important application of the present invention is to provide a novel treatment for patients suffering from HIV-1 or HTLV-I infection.

BRIEF DESCRIPTION OF THE FIGURES

FIG. 2 shows the results of in vivo expression studies using the IL-2 and IL-2R regulatory sequences and mutants thereof.

DETAILED DESCRIPTION OF THE INVENTION

Figure 1:
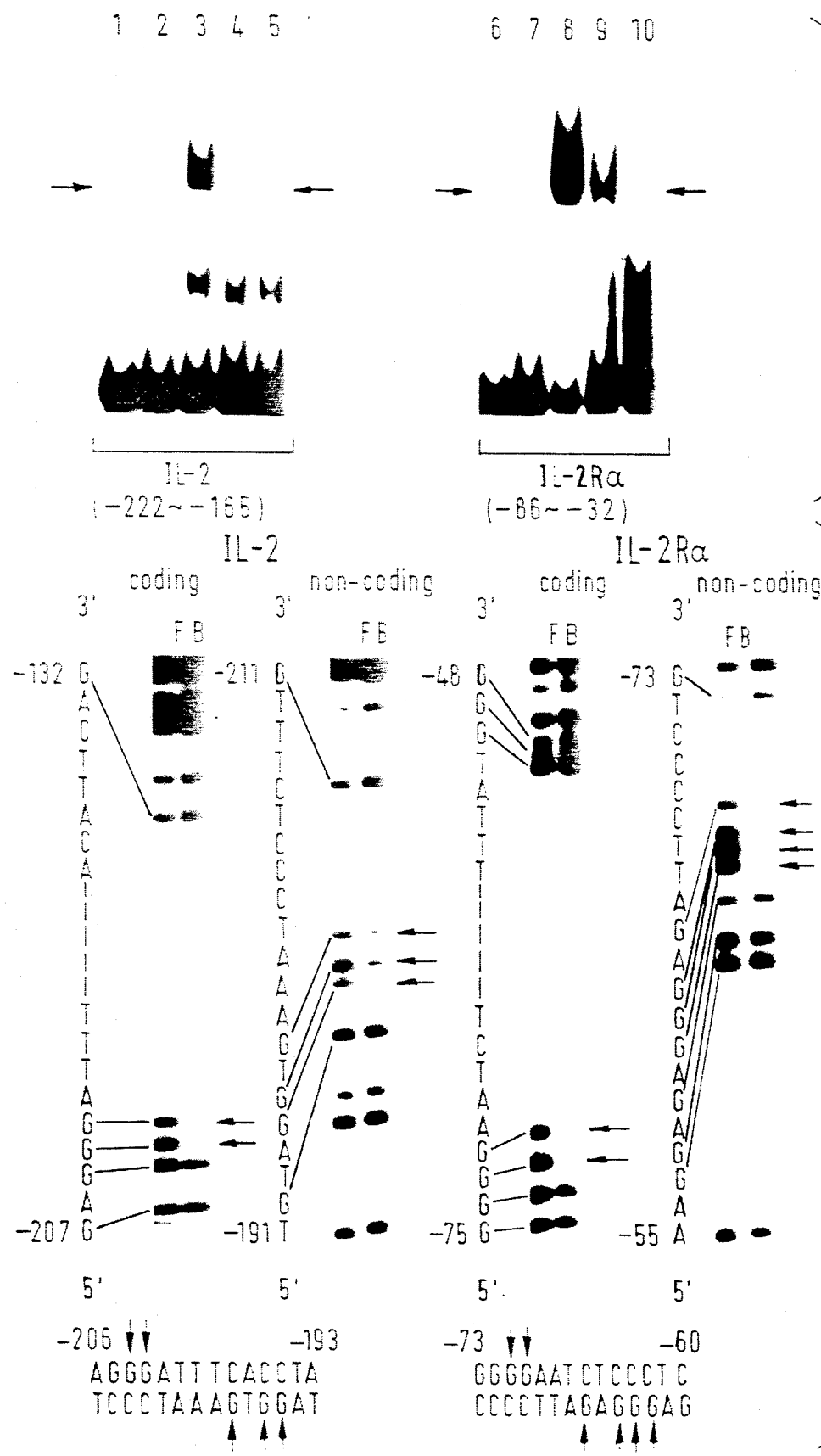
FIG. 1a shows the gel-retardation assays for the detection of a transcription factor that specifically binds to both IL-2 and IL-2R α sequences.
FIG. 1b shows the results for methylation interference studies to determine the contact regions of transcription factor in the IL-2 and IL-2R α sequences.

In accordance with the present invention we provide an novel DNA molecule comprising: a) a fragment of the IL-2 gene, said fragment comprising the sequence spanning from −195 to −204 of said IL-2 gene, and/or the sequence spanning from −115 to −164 of said IL-2 gene; and/or b) a fragment of the IL-2R α gene, said fragment comprising the sequence spanning from −62 to −71 of the said IL-2R α gene.

The DNA molecule described in the previous paragraph may also include: a) a fragment of the IL-2 gene wherein said fragment includes the sequence spanning from −165 to −222 of said IL-2 gene; and/or b) a fragment of the IL-2R α gene wherein said fragment includes the sequence spanning from −32 to −86.

The DNA molecule may comprise two or more repeat sequences of said fragment or fragments of said IL-2 gene and/or of said IL-2R α gene or said derivatives and mutants thereof. Suitably up to 15, up to 10, or up to 4 of said repeat sequences may be present.

The DNA molecule of this invention may be single stranded (ss) or double stranded (dd). The invention further provides an RNA fragment which contains a sequence capable of hybridizing to at least one of the DNA molecules described in the present invention and which is also capable of hybridizing to the LTR of HIV-1.

Preferably the RNA molecule further contains an additional nucleotide sequence capable of hybridizing to a DNA sequence within the LTR region of HIV-1. This additional fragment hybridizes to sequences adjacent to but not overlapping with the LTR regions which hybridize with the DNA molecules described in the invention.

It is recognized that molecules or fragments of DNA or RNA as described in this invention may be altered by deletion, addition or mutation. A mutation or mutant as defined herein is any change or number of changes that alter the sequence of bases along the DNA or RNA fragment. Therefore, derivatives of the DNA or RNA sequence are encompassed by the present invention as long as the sequences can bind to regulatory (transcription) factor(s) to inhibit or control retroviral replication, or inhibit or control the expression of IL-2 or IL-2R α genes.

A fragment as used herein refers to a part or portion of the nucleotide sequence in and around the gene of interest. The boundaries of these nucleic acids (two or more nucleotides) have been defined according to the nucleotide position, for example, −195 to −204.

The boundaries as defined in this invention are not to be exclusive and can vary at the 5' or 3' end of the nucleotide sequence as long as these sequence fragments can bind to regulatory (transcription) factor(s) to inhibit or control retroviral replication, or inhibit or control the expression of IL-2 or IL-2R α genes. In addition, a double stranded DNA and/or RNA molecule as defined herein may also contain single stranded overhanging ends at the 3' termini, the 5' termini or both.

A further aspect of the invention comprises a composition for inhibiting the replication of HIV-1 or HTLV-I virus comprising a DNA molecule or RNA fragment as defined in this invention or a derivative or mutant thereof.

A further aspect of the present invention comprises a method of determining the binding affinity of a test substance. Test substances may consists of the nuclear (transcription) factor, analogous artificial protein factor, or RNA fragment as described in the invention. Binding affinity test may also be preformed on a peptidomimetic to regulatory sequences including an IL-2 regulatory sequence (−165 to −222; and/or −115 to −164), an IL-2R α gene sequence (−32 to −86), or to a recognition site sequence in HIV-1 and HTLV-I DNA. This method of determining binding affinities comprises bringing a DNA molecule as defined in the present invention into contact with said test substance and then determining the efficiency with which binding has occurred, if at all.

The foregoing DNA molecules may be obtained either by digestion of naturally occurring DNA from any cell containing the IL-2 or IL-2R α genes, for example, Jurkat cells. These DNA molecules may also be produced through cDNA synthesis by reverse transcription of mRNA extracted from suitable cells, or by chemical synthesis of single stranded DNA followed by formation of double stranded DNA using techniques which are now well known in the art. The RNA fragments can also be prepared by methods well known in the art. (Maniatis et al., Molecular Cloning, A Laboratory Manual.)

Other suitable DNA molecules for the purposes of the present invention comprise double stranded DNA mutants of the aforementioned DNA sequences wherein one or more of the nucleotides is substituted by an altered nucleotide and/or the factor (recognition) binding site of the aforementioned DNA sequences is multimerized. Such mutant DNA is capable of binding a nuclear (transcription) factor which binds to one or the other of the aforementioned IL-2 or IL-2R α gene sequences.

One such mutant double stranded DNA has the sequence:

5' CTAGAGGGATTTCACCGAGGGATTTCACCGAGGGATTTCACCGAGGGATTTCACCG 3'
    TCCCTAAAGTGGCTCCCTAAAGTGGCTCCCTAAAGTGGGTCCCTAAAGTGGCCTAG 56MER
                                                              ×2 factor binding site (_____)

Thus it is possible to create, artificially, DNA sequences that efficiently bind to the transcription factors that are involved not only in binding recognition sequences of the IL-2 and IL-2R α genes but also involved in binding recognition sequences in HIV-1 and HTLV-I. These transcription factor(s) may also bind other genes in T lymphocytes as well as other cells. Thus, by competitively binding these factors, it is possible to block their ability to bind to IL-2 and IL-2R α genes as well as prevent their binding to recognition sequences in HIV-1 or HTLV-I. The result described here is merely given by way of example and it is possible to create DNA molecules which are even more efficient in binding these transcription factors.

The present invention also relates to RNA fragments capable of binding to the LTR of HIV-1 sequence. Such an RNA fragment may contain any number of nucleotides. for example, 30 nucleotides and may be blocked at the 5' end. The resulting RNA/DNA hybrid binds the regulatory (transcription) factor with reduced affinity or binding is blocked altogether. By designing the RNA molecule so that it is specific for the sequences adjacent to the recognition site of the LTR, binding to the recognition sequences of IL-2 or IL-2R α genes or other genes can be avoided or will occur with reduced affinity. This is possible because the sequences surrounding the recognition sites of IL-2 and IL-2R α differ from those surrounding the recognition sites in the LTR of HIV-1.

Specific nucleic acid fragments or molecules such as ssRNA, ssDNA and dsDNA molecules can be made with altered solubility characteristics, such as increased lipophilicity for easier penetration through biological membranes. Improved lipophilicity can be achieved by modifying the ribose or deoxyribose residues with lipophilic compounds, for example. terpene. The competitive nucleic acid fragments or molecules described in the present invention may also be obtained by using rare nucleotides or nucleotides analogues known in the art. Such artificial DNA or RNA sequence or multimeric forms thereof may be used for competitive titration of the regulator (transcription) factor(s) in the cell.

The nucleic acid molecules or fragments of the present invention open up the possibility of therapy of HIV-1 or HTLV-I infections by administration of DNA which will bind competitively to the factor(s) which induce viral replication such as tax-1. Therapy for HIV-1 or HTLV-I infection may also be accomplished by administering an RNA or artificial protein or fragment thereof, for example, a peptide or peptidomimetic which will bind to the LTR of HIV-1. The invention also makes it possible to carry out binding studies on synthetic binding proteins which will bind competitively to the said sequences of the cellular DNA without having inducing activity, thus in this way down regulating virus production.

The subject nucleic acids can be formulated into pharmaceutical compositions according to known methods of preparing pharmaceutically useful compositions. In this manner, the nucleic acids are combined in a mixture with a pharmaceutically acceptable carrier vehicle. Suitable vehicles and their formulation, including other human proteins, e.g., human serum albumin, are described, for example, in *Remington's Pharmaceutical Sciences* (16th ed., Osol, A., ed., Mack, Easton, Pa. (1980)). In order to form a pharmaceutically acceptable composition suitable for effective administration, such compositions will contain a therapeutically effective amount of the subject nucleic acids (an effective amount for controlling or inhibiting expression of IL-2 and IL-2R α genes as well as inhibiting or controlling HIV-1 or HTLV-I viral replication), together with a suitable amount of carrier vehicle.

The nucleic acids may be formulated as a sterile pharmaceutical composition for therapeutic use which is suitable for intravenous administration. The product may be in lyophilized form to be reconstituted for use by the addition of a suitable carrier, or diluent, or alternatively, it may be in the form of an aqueous solution.

For reconstitution of a lyophilized product in accordance with the present invention, one may employ a sterile diluent, which may contain materials generally recognized for approximating physiological conditions. In this manner, the sterile diluent may contain a buffering agent to contain a physiologically acceptable pH, such as sodium chloride, saline, phosphate-buffered saline, and/or other substances which are physiologically acceptable and/or safe for use.

When used as an aqueous solution, the pharmaceutical composition, for the most part, will contain many of the same substances described above for the reconstitution of a lyophilized product.

The nucleic acids useful in the methods of the present invention may be employed in such forms as, for example sterile suspensions for injection or encapsulated for targeting to specific tissue sites. The nucleotides may also be conjugated with antibodies directed to cell surface structures of T-cells or other cells which maybe infected with HIV-1 or HTLV-I. See, for example, Bevilacqua et al., *PNAS USA* 83:9238-9242 (1987); Cotran et al., *J. Exp. Med.* 164:661-666 (1986).

Where the subject nucleic acids are to be administered to a host for controlling or inhibiting expression of IL-2 and IL-2R α as well as inhibiting or controlling HIV-1 and HTLV-I viral replication, the nucleic acids may be administered, for example, intraarticularly, intraperitoneally, intrapleurally, intraocularly, by injection, subcutaneously, or the like. Administration by injection includes continuous infusion as well as single or multiple boluses.

The amount of the subject nucleic acid administered will vary with the manner of administration, the concurrent use of other active compounds, host size, type and severity of infection, and the like. Generally, the nucleic acids will be administered in sufficient doses to obtain a concentration of about 0.1 nM to about 100 nM, usually about 5 nM of the nucleotide in the blood. The dosage amount of nucleic acids necessary to obtain the desired concentration in the blood can be determined by pharmacokinetic studies using labeled nucleotides. Alternatively, in vivo studies on test animals, for example, monkeys may be used to determine effective dose ranges.

Additional pharmaceutical methods may be employed to control the duration of action. Controlled release preparations may be achieved through the use of polymers to complex or absorb the subject nucleic acids. The controlled delivery may be achieved by selecting appropriate macromolecules (for example, polyesters, polyamino acids, polyvinyl, polypyrrolidone, ethylenevinylacetate, methylcellulose, carboxymethylcellulose, or protamine sulfate). The appropriate concentration of macromolecules as well as the methods of incorporation may be determined using the above-mentioned pharmacokinetic or in vivo studies. In this manner release of the nucleic acids can be controlled.

Another possible method useful in controlling the duration of action by controlled release preparations is the incorporation of the subject nucleic acids into particles of a polymeric material such as polyesters, polyamino acids, hydrogels, poly(lactic acid), or ethylenevinylacetate copolymers.

Alternatively, instead of incorporating the subject nucleotides into polymeric particles, it is possible to entrap these materials in microcapsules prepared, for example, by coacervation techniques or by interfacial polymerization, for example, hydroxymethylcellulose or gelatine-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences* (1980).

The following examples are offered by way of illustration and not by way of limitation.

EXAMPLE 1

Mitogen-induced Binding of Nuclear Factor to the Regulatory Sequence Elements of Human IL-2 and IL-2R α Gene Nuclear extracts were prepared according to the method of Dignam et al. (Dignam, J. D. et al., *Nucleic Acids Res.* 11:1475–1489 (1983)), and the tel-retardation assay performed as previously described (Signh. H. et al., *Nature* 319:154–158 (1986); Fujita. T. et al., *EMBO J.* 7, in press (1988)). The $^{32}P$-labelled IL-2 DNA probe (phosphorylated at the 5'terminus of the coding strand) was prepared by isolating a 58 bp XbaI-DraI fragment from pIL2-222cat (Fujita. T. et al., *Cell* 46:401–407 (1986)). It encompasses the region from −165 to −222 with respect to the CAP site. The IL-2R α DNA probe was similarly prepared by isolating a 56 bp SalI-BamHI fragment from pIL-2R86cat. Essentially, the IL-2(R α probe encompasses the region from −32 to −86 with respect to the most upstream CAP site (Maruyama, M. et al., *Cell* 48:343–350 (1987)). Specific activity of the DNA was 3,000 c.p.m./f.mole in both probes. The unlabelled competitor DNAs were prepared similarly. Methylation interference analysis was carried out as described previously (Fujita, T. et al., *EMBO J.* 7, in press (1988)). The DNA probes were exactly the same as those described above, except that they were labelled at the 5' terminus of the coding or non-coding strand.

The results are presented in FIG. 1, wherein FIG. 1a shows gel-retardation assays for the detection of a factor that specifically binds to both IL-2 and IL-2R α sequences. Nuclear extracts (10 µg) from unstimulated or mitogen-stimulated Jurkat cells (1 µg/ml PHA, 50 ng/ml TPA for 3 hrs) were incubated with either IL-2 or IL-2R α DNA probe alone (3 f.moles) or in the presence of unlabelled competitor DNAs. Lanes 1 to 5 contain the IL-2 DNA probe, while lanes 6 to 10 contain the IL-2R α probe. Lanes 1 and 6, no extract; Lanes 2 and 7, extract from uninduced cells (−); Lanes 3 and 8, extract from induced cells (+); Lanes 4 and 9, extract (+) and unlabelled IL-2 DNA (1.2 p.mole); Lanes 5 and 10, extract (+) and unlabelled IL-2R α DNA (1.2 p.mole); FIG. 1b shows the results for methylation interference analysis for the factor contact regions of the IL-2 and IL-2R α DNAs. The left panel shows the analysis of the coding and noncoding strand of the IL-2 probe and the right panel, the analysis of the IL-2R α probe. The positions of methylated guanine residues that interfered with the factor binding are marked.

Using the gel-retardation assay at least three nuclear (transcription) factors were detected in a human T cell line, Jurkat that specifically bind to regulator elements within the 5'flanking region of the human IL-2 gene. The three factors recognize distinct DNA sequences. The DNA binding activities of two such factors were found to be induced in the mitogen-stimulated cells. The specific binding of one of the factors to the IL-2 gene sequence spanning from −165 to −222 was also inhibited by a molar excess of a DNA segment of the human IL-2R α regulatory sequences spanning from −32 to −86. Reciprocally, the factor binding to the IL-2R α DNA was inhibited by the IL-2 DNA segment (FIG. 1a). Other inducible factor(s) bound to the IL-2 sequence spanning from −115 to −164 and this binding was not affected by any of the tested IL-2R α sequences. The consensus sequences recognized by the factor were not obvious; examination of the factor contact sites of both DNA segments by methylation interference assay revealed as shown in FIG. 1b, that the contact regions of the factor were −195 to −204 and −62 to −71 for the IL-2 and IL-2R α genes, respectively. The contact region of the IL-2R α gene shows remarkable sequence similarity to the binding sites of NF- B that binds to an Igκ gene enhancer element (Sen, R. et al., *Cell* 46:705–716 (1986)). The corresponding region of the IL-2R α gene and a sequence within the HIV LTR also bind a transcription factor (NF- B-like factor or HIVEN86A) (Nabel, G. et al., *Nature* 326 711–713 (1987); Böhnlein, E. et al., *Cell* 53:827–836 (1988): Leung, K. et al., *Nature* 333:776–778 (1988)). Unexpectedly, we have found that the same factor binds to the 10 bp sites of this regulator sequence of IL-2.

EXAMPLE 2

To examine extent to which the factor binding to the above sequence elements influences the induced gene expression and the effect of various mutations within the factor contact region of the IL-2 and IL-2R α genes, various mutations within the elements were introduced and the functional properties of the mutant genes were analyzed using a strategy as follows:

Vector constructions were carried out essentially as described previously (Maruyama, M. et al., *Cell* 48:343–350 (1987)). To generate the mutations, the IL-2 or IL-2R α sequences were once cloned into a M13 phage vector and subjected to the oligonucleotide-directed mutagenesis as described by Kunkel et al., (Kunkel, T. A. et al., *Methods in Enzymology* 154:367–382 (1987)). Nucleotide sequences of the mutant DNAs were confirmed by sequence analyses. The reference gene, pRSVTK essentially contains the RSV LTR sequence linked to the HSV tk gene in the pRSVcat backbone DNA (Gorman, C. et al., *Proc. Natl. Acad. Sci. USA* 79:6777-6781 (1982)). The tax-1 expression vector, pCDS contains the HTLV-I-pX coding sequence that is abutted downstream to the CMV promoter/enhancer sequences in the vector H3M (Aruffo, A. et al., *Proc. Natl. Acad. Sci. USA* 84:8573-8577 (1987)). The DNA transfection, mitogen stimulation, RNA preparation and S1 analysis were carried out essentially as described previously (Maruyama, M. et al., *Cell* 58:343-350 (1987)). In determining the relative inducibilities by the S1 analysis of mRNAs, the induced mRNA levels were normalized by the tk specific mRNA levels in each sample (the tk mRNA levels did not differ significantly from one sample to the other).

Referring to FIG. 2 the IL-2 and IL-2R α regulatory sequences were respectively excised out of pI319Bcat and pRBXBcat (Maruyama, M. et al., *Cell* 58:343-350 (1987)) and they were each introduced into pSVOcat (Gorman, C. et al., *Mol. Cell. Biol.* 2:1044-1051 (1982)) as depicted in FIG. 2. Mutant genes were similarly constructed as described below. The genes were each cotransfected into Jurkat cells with a reference gene, pRSVtk. The cells were then treated by mitogens. Alternatively, the vector DNAs were transfected with a tax-1 expression vector pCDS and the cells were not treated by mitogen. The gene expression level was monitored by S1 analysis of the induced mRNA. Assuming that 1% of the transfected cells had received DNAs, the induced mRNA levels were about 250 and 100 strands per cell in the mitogen-stimulated cells and the tax-1-expressing cells, respectively in the case of the IL-2 gene (pSI319cat). In the case of the IL-2R α gene (pSRBXcat) the values were respectively about 150 and 100 strands per cell. The values of pSRBXcat are significantly lower than those of pRPXBcat, due to the absence of additional upstream elements (Maruyama, M. et al., *Cell* 48:343-350 (1987)). The transfection experiments were repeated three times and the results were reproducible. Always in the absence of mitogen stimulation or tax-1 expression, no specific mRNA was detectable in the transfected cells.

In this series of mutants, we thus included mutants in which the 10 bp IL-2 gene element was replace with the corresponding 10 bp element of either the IL-2R α or the Igκ gene ("sequence swapping" experiments). In this experiment, we also examined the effect of HTLV-I-derived transactivator, tax-1 on the expression of those genes. The tax-1 (p40$^x$, tax-1) has been shown to activate the IL-2 and IL-2Rα genes without extracellular mitogenic stimulation of T cells (Maruyama, M. et al., *Cell* 48:343-350 (1987); Inoue, J. et al., *EMBO J.* 5:2883-2888 (1986); Cross, S. L. et al., *Cell* 49:47-56 (1987); Siekevitz, M. et al., *Proc. Natl. Acad. Sci. USA* 84:5389-5393 (1987)). A significant reduction of the mitogen and tax-1 induced gene expression was observed with the IL-2 and IL-2R α genes each carrying mutations within the factor contact region. On the other hand, the IL-2 mutant genes each possessing the swapped sequence element gave rise to higher induction levels compared to the wild-type gene.

EXAMPLE 3

The upregulation of the IL-2 mutant genes was investigated by examining the binding affinities of the factor to the wild-type and mutant genes. A series of gel-retardation assays were preformed by using the factor extract and the IL-2 gene segments each containing either the wild-type or the swapped elements and the results are presented in FIG. 3, which shows that the Jurkat-derived factor binds the IL-2, IL-2R α and Igκ elements with different affinities.

Figure 3A:
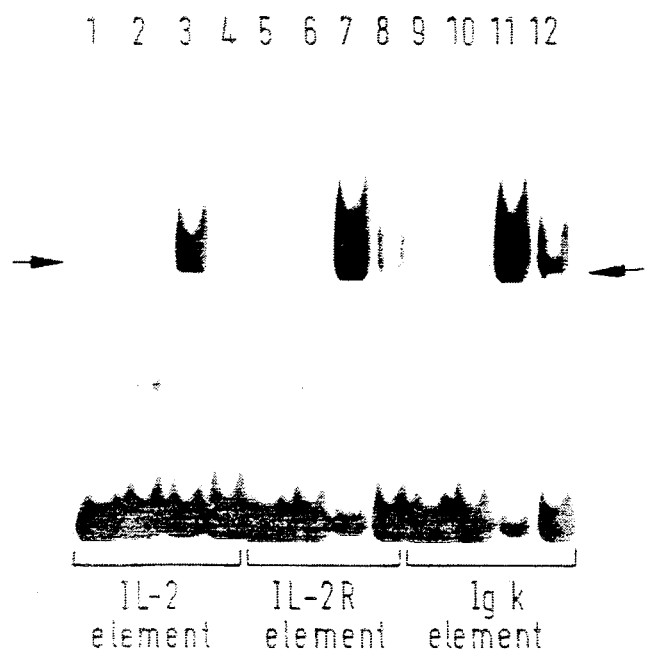
FIG. 3a shows the results of the gel-retardation analysis of the wild-type and mutant IL-2 DNA sequences with the nuclear extracts from the mitogen-stimulated Jurkat cells.

In particular FIG. 3a shows the results of gel-retardation analysis of the wild-type and mutant IL-2 DNA segments with the nuclear extracts from the mitogen-stimulated Jurkat cells. Fifty-two bp DNA segments of either wild-type (lanes 1-4) (spanning from −222 to −173) or the similar DNAs containing the swapped IL-2R α (lanes 5-8) or Igκ (lanes 9-12) elements were chemically synthesized and subjected to the analysis exactly as described in FIG. 1. Lanes 1, 5, 9; probe DNA. Lanes 2, 6, 10; probe DNA and extract from unstimulated cells. Lanes 3, 7, 11; probe DNA and extract from mitogen-stimulated cells. Lanes 4, 8, 12; same as lanes 3, 7, 11; except that each sample received 400 fold molar excess of the unlabelled wild-type IL-2 DNA segment.

FIG. 3 shows inhibition of complex formation between the factor and wild-type IL-2 DNA by the DNAs each containing the factor recognition element of either IL-2 or IL-2R α or Igκ gene. Gel-retardation assays were performed with the labelled wild type IL-2 DNA segment as described above. The DNAs were exactly the same as described above. The efficacy of formation of factor-DNA complexes were quantitated by densitometric analysis of the autoradiogram. Complex formation in the absence of competitor DNAs was taken as 100%.

Figure 3B:
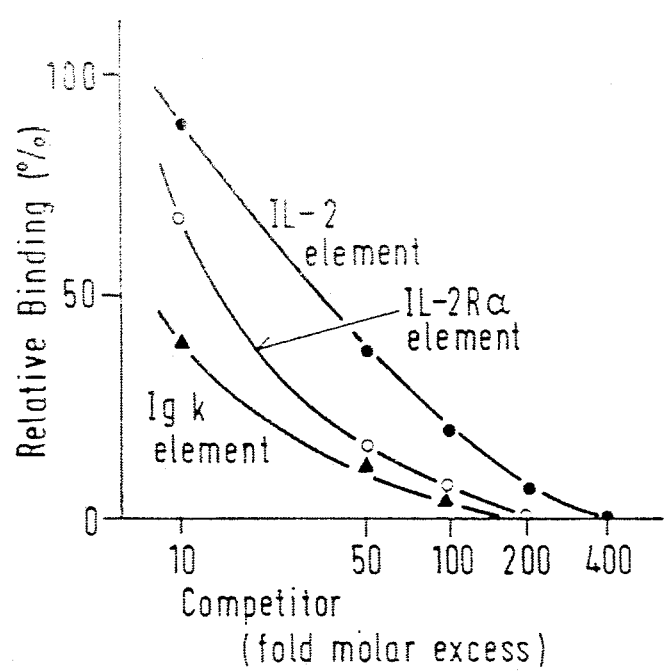
FIG. 3b shows the relative binding affinities of the transcription factor to the following DNA sequence elements: Igκ; IL-2R α; and IL-2.

More particularly in FIG. 3a it is shown that the gel mobilities of the shifted bands were indistinguishable from each other, evidencing that the same factor is bound to each of the elements. Moreover, under identical assay conditions, the intensity of the bands was significantly different and followed in increasing order Igκ, IL-2R α (IL-2 respectively. Next, a DNA competition assay was carried out in which the degree of complex formation between the factor and the $^{32}p$-labelled, wild-type IL-2 gene segment was analyzed in the presence or absence of unlabelled IL-2 gene segments. As shown in FIG. 3b, the affinities of the factor to those DNA sequences are in the order of Igκ, IL-2R α and IL-2 elements. Thus, the observed upregulation of the mutant genes may be attributed to a higher binding affinity of the factor to the Igκ and IL-2R α elements. As expected, the factor showed greatly reduced affinities to the genes with down-mutations factor. Significantly, the sequence elements of the human and murine IL-2 genes are identical, suggesting the importance of strict conservation of the element in controlling gene expression. These findings show that the gene expression level is a function of the binding affinity of the fragment to the regulatory element(s).

The induced expression of the IL-2 and IL-2R α genes thus involves a common transcription factor whose binding activity to both genes increases in mitogen-stimulated Jurkat T cells. We have noticed that the binding activity becomes almost undetectable following cycloheximide treatment at the onset of mitogen stimulation, suggesting the requirement of the de novo synthesis of this factor.

Interestingly, similar sequence elements are noticeable within the promoter region of many lymphokine genes as well as the LTR regions of lymphotropic retroviruses (Table 1). In view of the considerable sequence divergence in the contact sites of the factor as described above, this factor is acting also on the above listed genes as a "universal" regulatory factor. In this context, it is worth noting that many if not all of the listed genes are also activated by tax-1 (Maruyama, M. et al., *Cell* 48:343–350 (1987); Inoue, J. et al., *EMBO J.* 5:2883–2888 (1986); Cross, S. L. et al., *Cell* 49:47–56 (1987); Siekevitz, M. et al., *Proc. Natl. Acad. Sci. USA* 84:5389–5393 (1987); Yoshida, M. et al., *Ann. Rev. Immunol.* 5:541–559 (1987); Siekevitz, M. et al., *Science* 238:1575–1578 (1987); Miyatake, S. et al., *Nucleic Acids Res.* 16:6547–6566 (1988)).

EXAMPLE 4

In order to examine whether the IL-2 regulatory sequence that is bound by the transcription factor is useful in (i) detection of the factors that bind to the similar sites in other genes, and (ii) titration of the factor by DNA sequences which efficiently bind to the factor (useful in the selective inhibition of certain gene expression), a piece of double stranded DNA was chemically synthesized as depicted below. The DNA consists of two strands each consisting of 56 nucleotides. The double stranded DNA contains four repeats of the factor binding site. It is possible to create a variety of similar DNA, in order to increase the binding efficiency to the factor.

```
5' CTAGAGGGATTTCACCGAGGGATTTCACCGAGGGATTTCACCGAGGGATTTCACCG 3'
   TCCCTAAAGTGGCTCCCTAAAGTGGCTCCCTAAAGTGGCTCCCTAAAGTGGCCTAG   56mer
                                                               ×2
``` factor binding site (_____)

(1) When this DNA was used as a competitor DNA in a gel shift analysis as described in FIG. 1a, the appearance of the shifted band, which reflects the complex formed between the factor and the IL-2 DNA (labelled by $^{32}P$), was completely inhibited by the unlabelled, molar excess of the above DNA. This demonstrates that the above DNA binds to the factor.

(2) When the above DNA was $^{32}P$ labelled and used as the probe to perform the gel shift assay under exactly the same assay conditions as described in FIG. 1a, the specific complex with the DNA and the factor was also obtained. This complex formation was inhibited by the molar excess of the IL-2 and IL-2 α receptor DNA sequences containing the factor binding site. The results corroborate the result presented in (i), that the above DNA can bind to the factor. Furthermore, in the gel shift analysis, an additional band is seen in the gel shift assay, indicating that the DNA can bind more than two of the factors (since the above DNA contains multiple factor binding sites).

(3) When the above DNA was linked to the IFN promoter, exactly as described with reference to FIG. 2, instead of the natural IL-2 and IL-2 α receptor DNA sequences, and assayed for the inducibility of the reporter CAT gene by transfecting the constructed DNA into Jurkat cells (the cells were subsequently induced by mitogens as described above), very efficient induction of the CAT gene was observed. In fact, the inducibility was about 15 times higher compared to the similar construct containing the natural IL-2 sequence (in FIG. 2, it is pSIR319cat).

Thus it is possible to create, artificially, DNA and other sequences that efficiently bind the transcription factor which is involved in the recognition of IL-2 and IL-2 α receptor genes, and of other genes in T lymphocytes and other cells as well as recognition sites in the HIV-1 and HTLV-I. The results described here are given by way of example and it is possible to create even more efficient DNA that bind to the factor, thereby blocking the factors binding to IL-2 and IL-2 α receptor genes and the other aforementioned recognition sequences.

I claim:

TABLE 1

Presence of factor recognition sites within promoter, LTR regions of the genes expressed in T cells.

| | | | ref. |
|---|---|---|---|
| IL-2 | (human)* | $-^{204}$GGATTTCACC$-^{195}$ | Fujita, T. et al. Cell 46, 401–407 (1986). |
| IL-2R α | (human)* | $-^{71}$GGAATCTCCC$-^{62}$ | Maruyama, M. et al. Cell 48, 343–350 (1987). |
| IFN-γ | (human) | $-^{233}$GAATCCCACC$-^{224}$ | Gray, P. W. & Goeddel, D. V. Nature 298, 859–863 (1982). |
| IL-6 | (human) | $-^{134}$GGATTTTCCC$-^{125}$ | Yasukawa, K. et al. EMBO J. 6, 2939–2945 (1987). |
| IL-3 | (mouse) | $-^{295}$GAGATTCCAC$-^{286}$ | Miyatake, S. et al. Proc. Natl. Acad. Sci. USA 82, 316–320 (1985). |
| IL-4 | (mouse) | $-^{190}$GGTGTTTCAT$-^{181}$ | Otsuka, T. et al. Nucleic Acids Res. 15, 334–344 (1987). |
| GM-CSF | (mouse) | $-^{104}$GAGATTCCAC$-^{95}$ | Stanley, E. et al. EMBO J. 4, 2569–2573 (1985). |
| c-fos | (human) | $-^{278}$GGCCTTTCCC$-^{269}$ | Van Straaten, F. et al. Proc. |

TABLE 1-continued

Presence of factor recognition sites within promoter. LTR regions of the genes expressed in T cells.

| | | ref. |
|---|---|---|
| HIV LTR* | $-^{89}$GGGACTTTCC$^{-80}$<br>$-^{103}$GGGACTTTCC$^{-94}$ | Natl. Acad. Sci. USA 80, 3183-3187 (1983).<br>Starchch, H. et al. Science 227, 538-540 (1985). |
| HTLV-I LTR | $+^{168}$GGAGCCTACC$^{+177}$<br>$-^{244}$GACGTCTCCC$^{-235}$ | Seiki, M. et al. Proc. Natl. Sci. USA 80, 3618-3622 (1983). |

*Factor binding has been demonstrated.

1. A DNA molecule comprising a fragment of the IL-2 gene, said fragment spanning from $-195$ to $-204$ of the genetic sequence of said gene and mutants thereof.

2. A DNA molecule comprising a fragment of the IL-2 gene, said fragment spanning from $-115$ to $-164$ of the genetic sequence of said gene and mutants thereof.

3. A DNA molecule comprising two fragments of the receptor (IL-2R) α gene, said fragment spanning from $-62$ to $-71$ of the genetic sequence of said gene and mutants thereof.

4. A DNA molecule comprising a fragment of the IL-2 gene, said first fragment spanning from $-195$ to $-204$ of the genetic sequence of said gene, and said second fragment spanning from $-115$ to $-164$ of the genetic sequence of said gene and mutants thereof but specifically lacking a substantial portion of the fragment spanning from $-165$ to $-194$ of the genetic sequence of said gene.

5. A DNA molecule comprising a fragment of the IL-2 gene and a fragment of the IL-2R α gene, said first fragment spanning from $-195$ to $-204$ of the genetic sequence of said IL-2 gene, and said second fragment spanning from $-62$ to $-71$ of the genetic sequence of said IL-2R α gene and mutants thereof.

6. A DNA molecule comprising a fragment of the IL-2 gene and a fragment of the IL-2R α gene, said first fragment spanning from $-115$ to $-164$ of the genetic sequence of said IL-2 gene, and said second fragment spanning from $-62$ to $-71$ of the genetic sequence of said IL-2R α gene and mutants thereof.

7. The DNA molecule of claim 4 further comprising a fragment of the IL-2R α gene, said fragment spanning from $-62$ to $-71$ of the genetic sequence of said gene and mutants thereof.

8. A DNA molecule comprising a fragment of the IL-2 gene, said fragment spanning from $-165$ to $-222$ of the genetic sequence of said gene and mutants thereof.

9. A DNA molecule comprising a fragment of the receptor (IL-2R) α gene, said fragment spanning from $-32$ to $-86$ of the genetic sequence of said gene and mutants thereof.

10. A DNA molecule comprising a fragment of the IL-2 gene and a fragment of the IL-2R α gene, said first fragment spanning from $-165$ to $-222$ of the genetic sequence of said IL-2 gene, and said second fragment spanning from $-32$ to $-86$ of the genetic sequence of said IL-2R α gene and mutants thereof.

11. A DNA molecule as defined in claims 1, 2, 3, 4, 5, 6, 7, 8, 9, or 10 which is a double stranded DNA molecule.

12. A DNA molecule as defined in claims 1, 2, 3, 4, 5, 6, 7, 8, 9, or 10, comprising two or more of at least one of said fragments.

13. A DNA molecule as defined in claim 12 which is a double stranded DNA molecule.

14. A DNA molecule as defined in claim 12, containing up to 15 of at least one of said fragments.

15. A DNA molecule as defined in claim 14 which is a double stranded DNA molecule.

16. A DNA molecule as defined in claim 14, containing up to 10 of at least one of said fragments.

17. A DNA molecule as defined in claim 16 which is a double stranded DNA molecule.

18. A DNA molecule as defined in claim 16, containing up to 4 of at least one of said fragments.

19. A DNA molecule as defined in claim 18 which is a double stranded DNA molecule.

20. A RNA fragment comprising a sequence capable of stably hybridizing at least one of the DNA sequences as defined in claims 1, 2, 3, 4, 5, 6, 7, 8, 9, or 10.

21. An RNA fragment defined in claim 20 which is capable of stably hybridizing to the LTR region of HIV-1.

22. An RNA fragment comprising a sequence capable of stably hybridizing to at least one of the DNA sequences as defined in claim 1, 2, 3, 4, 5, 6, 7, 8, 9, or 10, said RNA fragment also being capable of stably hybridizing to the LTR region of HIV-1, said RNA fragment which further contains an additional nucleotide sequence, said sequence being capable of hybridizing to a region adjacent to the LTR region of HIV-1.

* * * * *